United States Patent
Sharma et al.

(10) Patent No.: US 11,422,138 B2
(45) Date of Patent: Aug. 23, 2022

(54) DETECTION AND TREATMENT OF PREGNANCY COMPLICATIONS COMPRISING DETERMINING SIALYL LEWIS ANTIGENS AND ADMINISTERING HCG

(71) Applicant: Women & Infants Hospital of Rhode Island, Providence, RI (US)

(72) Inventors: Surendra Sharma, Warwick, RI (US); Satyan Kalkunte, Frisco, TX (US); Udo Jeschke, Munich (DE)

(73) Assignee: Women & Infants Hospital of Rhode Island, Providence, RI (US)

( * ) Notice: Subject to any disclaimer, the term of this patent is extended or adjusted under 35 U.S.C. 154(b) by 66 days.

(21) Appl. No.: 16/777,444

(22) Filed: Jan. 30, 2020

(65) Prior Publication Data

US 2020/0166527 A1    May 28, 2020

Related U.S. Application Data

(63) Continuation of application No. 15/889,261, filed on Feb. 6, 2018, now Pat. No. 10,585,106, which is a continuation of application No. 14/438,033, filed as application No. PCT/US2013/067032 on Oct. 28, 2013, now abandoned.

(60) Provisional application No. 61/739,817, filed on Dec. 20, 2012, provisional application No. 61/721,228, filed on Nov. 1, 2012.

(51) Int. Cl.
| | |
|---|---|
| *G01N 33/76* | (2006.01) |
| *G01N 33/68* | (2006.01) |
| *A61K 38/24* | (2006.01) |

(52) U.S. Cl.
CPC ............ *G01N 33/76* (2013.01); *A61K 38/24* (2013.01); *G01N 33/689* (2013.01); *G01N 2400/10* (2013.01); *G01N 2440/38* (2013.01); *G01N 2800/368* (2013.01)

(58) Field of Classification Search
None
See application file for complete search history.

(56) References Cited

U.S. PATENT DOCUMENTS

2011/0166030 A1    7/2011 Wang et al.

FOREIGN PATENT DOCUMENTS

WO    2012024543    2/2012

OTHER PUBLICATIONS

Baha Sibai, American Journal of Obstetrics & Gynecology, 2007; doi: 10.1016/j.ajog.2007.04.021; 2 pages total (Year: 2007).*
Wang, et al., "D2-40/podoplanin expression in the human placenta.", Placenta. Jan. 2011, 32(1): 27-32.
International Application No. PCT/US2013/067032 International Search Report dated Jan. 17, 2014.
International Preliminary Report on Patentability dated May 5, 2015, issued in corresponding International Application No. PCT/US2013/067032.
Norris, et al., American Journal of Reproductive immunology 65 (Suppl. 1); published Jun. 2011: 8-28; see p. 17, abstract #T18 (Year: 2011).
Tutunaru, et al., International Congress Series, 2004; 1271; 367-371 (Year: 2004).
Sharma; Abstract PL4; Placenta 31; 2010; A.1-A 137 (Year: 2010).
Minas, et al., Histochem Cell Biol. 2007; 128:55-63 (Year: 2007).
Jeschke, et al., Anticancer Research, 2003; 23: 1087-1092 (Year: 2003).
Mellembakken, et al., Hypertension; 2002; 39: 155-160 (Year: 2002).
O'Loughlin, et al., "The Diagnosis and Management of Pre-eclampsia and Eclampsia," Institute of Obstetricians and Gynaecologists, Royal College of Physicians of Ireland; Version 1.0 Guideline No. 3, published Sep. 2011 (Year: 2011).
Kalkunte, et al., American Journal of Reproductive Immunology, 2012; 67 (Suppl. 2): Abstract P020, p. 53 (Year: 2012).
The website downloaded Dec. 18, 2018 from https://www.webmd.com/baby/preeclampsia-risk?print=:true, 3 pages total (Year: 2018).

* cited by examiner

*Primary Examiner* — Christina M Borgeest
(74) *Attorney, Agent, or Firm* — Saul Ewing Arnstein & Lehr LLP; Brian R. Landry; Justin W. Crotty

(57) ABSTRACT

Disclosed herein is a method of identifying and/or addressing incipient preeclampsia in a patient-subject by the steps of (a) performing a bioassay to determine the level of at least one sialyl Lewis antigen in a said patient-subject at about 25 weeks of pregnancy or earlier; (b) performing a bioassay to determine the level of at least one sialyl Lewis antigen in a pregnant non-preeclampsia one or more subjects at about 30 weeks of pregnancy or later, wherein said at least one sialyl Lewis antigen assay is for a sialyl Lewis antigen assayed in step (a) is and if more than one subject is assayed, averaging said results; and (c) managing said patient-subject for preeclampsia, if said level of at least one sialyl Lewis antigen of step (a) is at or greater than about 20% above the level of such sialyl Lewis antigen assayed in step (b).

6 Claims, 2 Drawing Sheets

DETECTION AND TREATMENT OF PREGNANCY COMPLICATIONS COMPRISING DETERMINING SIALYL LEWIS ANTIGENS AND ADMINISTERING HCG

RELATED APPLICATION DATA

This application is a continuation of U.S. application Ser. No. 15/889,261, filed Feb. 6, 2018, which is a continuation of U.S. application Ser. No. 14/438,033, filed Apr. 23, 2015, which is the U.S. national phase pursuant to 35 U S C. § 371, of International application Ser. No. PCT/US2013/067032, filed Oct. 28, 2013, which claims the benefit of U.S. provisional application Ser. No. 61/721,228, filed Nov. 1, 2012, and 61/739,817, filed Dec. 20, 2012. The entire disclosures of the aforementioned patent applications are incorporated herein by reference.

FIELD OF THE INVENTION

The present invention relates to a method of identifying and/or addressing incipient preeclampsia in a patient-subject by the steps of (a) performing a bioassay to determine the level of at least one sialyl Lewis antigen in a said patient-subject at about 25 weeks of pregnancy or earlier, (b) performing a bioassay to determine the level of at least one sialyl Lewis antigen in one or more pregnant non-preeclampsia subjects at about 30 weeks of pregnancy or later, wherein said at least one sialyl Lewis antigen assay is for a sialyl Lewis antigen assayed in step (a) is and if more than one subject is assayed, averaging said results; and (c) managing said patient-subject for preeclampsia, if said level of at least one sialyl Lewis antigen of step (a) is at or greater than about 20% above the level of such sialyl Lewis antigen assayed in step (b).

Particular reference is made to sialyl Lewis type antigens on glycoproteins.

Also noted are assays performed in liquid samples. A particular immunoassay is used as diagnostic tool to predict onset of pregnancy complications including preeclampsia and HELLP syndrome (i.e., a group of symptoms that occur in pregnant women characterized by hemolysis, elevated liver enzymes, and low platelet count). A further aspect is use of glycoprotein devoid of blood group sialyl Lewis type antigens to rescue, prevent or treat preeclampsia-like symptoms.

BACKGROUND

The following abbreviations are used herein:
BMDC—bone marrow derived dendritic cells
hCG—human chorionic gonadotropin
HhCG—hyperglycosylated hCG
IDO—indoleamine 2,3-dioxygenase
IFN-γ—interferon gamma
Tregs—regulatory T cells
Th17—T helper 17 cells
TGF—transforming growth factor
TF—Thomsen-Friedenreich antigen
uNK—natural killer cells
IL-10 Interleukin 10 VEGF C—Vascular endothelial growth factor C
VEGF C—Vascular endothelial growth factor C
NPS—normal pregnancy serum
PE preeclampsia
PES preeclampsia serum
sEng—soluble endoglin
GPs—gestational pathologies.

Pregnancy is a dynamic process characterized by immune tolerance, angiogenesis, and hormonal regulation. Human chorionic gonadotropin (hCG) is reported as detected on the first day of implantation; its levels peak around gestational week 12 and diminish to low levels during the remainder of pregnancy. hCG is believed to exhibit a number of functions in pregnancy, including the promotion of progesterone production, implantation and decidualization, angiogenesis, cytotrophoblast differentiation, and immune cell regulation. With these myriad functions in mind, hCG dysregulation could lead to adverse pregnancy outcomes. Preeclampsia is a condition marked by insufficient trophoblast invasion and maternal spiral artery remodeling and inflammation. Recent studies have reported a link between preeclampsia and immune cell dysregulation, including reduced numbers of uterine and circulating regulatory T cells (Tregs) and natural killer (uNK) cells.

Managing women for preeclampsia is a topic widely addressed in the art. By way of non-limiting example, reference is made to *The Diagnosis and Management of Pre-eclampsia and Eclampsia*, O'Loughlin et al. (Institute of Obstetricians and Gynaecologists, Royal College of Physicians of Ireland (Version 1.0. Guideline No. 3, 2011).

hCG Variants hCG is composed of a and β subunits each consisting of a protein backbone with N-linked and O-linked oligosaccharides. It is now believed that there are four distinct variants: hCG, hyperglycosylated hCG (HhCG), the free β-subunit, and pituitary hCG. These four can be further modified by partial degradation of the hCG molecule, nicking of the intact β-subunit, or variation of the attached Oligosaccharides These variants play different roles in both normal and abnormal pregnancy. HhCG, has complex β-subunit N- and O-linked oligosaccharides structural alterations. HhCG is produced early normally during pregnancy; it does not have high affinity to LH/hCG receptors, yet is reported to promote invasion and growth of cytotrophoblasts by interacting with transforming growth factor (TGF) β receptors. After the initial three to four weeks of pregnancy, the levels of HhCG become very low and hCG (non-hyperglycosylated) is usually the predominant form Recent studies have reported additional variants with distinct sialylated oligosaccharides of the Lewis type pattern on hCG isolated from serum of pregnant women. Differential expression of such carbohydrates is associated with inhibition of E-selectin-mediated homing of leukocytes and may contribute to early pregnancy loss through poor placental-immune interactions. Without being bound by any particular theory, it is believed that in the time between placentation and parturition a dynamic structural conversion of one form of hCG to alternate forms of hCG is choreographed. This suggests that impairment or alterations in hCG glycosylation patterns affect its signaling and biological activities.

hCG, Angiogenesis and Immune Tolerance

The maternal-fetal interface is replete with immune cells which cross-talk with hormonal, endocrine, and angiogenic regulators to program a normal pregnancy outcome. Among immune cell types, regulatory T cells a specialized CD4 T cell subset phenotyped as CD4+CD25+/Foxp3+, play an important role in protecting the fetus by dampening harmful inflammatory immune responses at the maternal-fetal interface. It has been shown in humans that Treg numbers increase very early in pregnancy, peak during the early second trimester and then begin to decline until they reach pre-pregnancy levels. Tregs have also been described as significant in immune tolerance of the fetus in the mouse pregnancy model. Tregs have been described as following a gestational age-dependent presence in the uterus. Animal studies further indicate that tolerance to paternal antigens may be initiated during mating when seminal fluid and components of semen have been shown to trigger expansion of the Treg cell population. Further, it has been reported that Tregs migrate toward areas of hCG production, indicating that in normal pregnancy, these cells may be attracted to hCG produced by trophoblasts at the maternal-fetal interface ensuring immune tolerance of the fetus. However, if hCG undergoes dysregulation during pregnancy, its control over immune tolerance pathways may be impaired. Interleukin-10 (IL-10) and the tryptophan-metabolizing enzyme indoleamine 2,3-dioxygenase (IDO) are two specific immune regulators Levels of IL-10, an immunosuppressant, reportedly increase in early pregnancy and remain elevated until the onset of labor, possibly regulating maternal immunity and allowing acceptance of the fetal allograft. IL-10 reportedly regulates uNK cell maintenance and further controls their cytotoxic functions in response to pro-inflammatory challenges during pregnancy. Further, decidual Tregs reportedly inhibit immune stimulation of T cells through IL-10 production. It is believed that the temporal expression of IDO regulates the Tregs and prevents them from being converted to pro-inflammatory Th17 cells hCG reportedly stimulates IL-10 production of murine BMDC. This same study found that treatment of BMDC with hCG and interferon gamma (IFN-γ) increased IDO mRNA production and enzyme activity.

It is noteworthy that hCG is now considered as an angiogenic factor and thus may regulate an endovascular cross-talk between trophoblasts, endothelial cells, and immune cells represented by uNK cells. In animal studies these specialized cells have been reported as playing a role in spiral artery remodeling and trophoblast invasion Vascular endothelial growth factor C (VEGF C) production by uNK cells is responsible for their non-cytotoxic activity, and that VEGF C producing uNK cells support endovascular processes in vitro. It is possible that the tolerogenic phenotype of uterine NK cells during early decidualization is be influenced by hCG through stimulation of the quiescent angiogenic machinery. Recent studies indicate that the uNK cells are indeed influenced by hCG. One study reported that hCG induces proliferation of human uNK cells, by interacting through the mannose receptor rather than the LH/hCG receptor.

hCG and Preeclampsia

Some reports define preeclampsia as hypertension in a previously normotensive pregnant female and proteinuria after 20 weeks of pregnancy (or gestation). Preeclampsia affects 5-10% of all pregnancies and remains a leading cause of maternal and fetal morbidity and mortality. Related gestational pathology include Intrauterine growth restriction, eclampsia, gestational hypertension (i.e., hypertension in pregnancy without proteinuria) broadly termed "gestational pathologies" ("GPs").

Based on clinical presentation, preeclampsia is considered as a late pregnancy disorder. Molecular events leading to its onset seem to occur earlier in pregnancy Portrayed as a two stage disorder, maternal symptoms of preeclampsia are classified as consequences of pre-clinical placental pathology associated with poor placental perfusion, inflammation, ischemia/hypoxia, and trophoblast damage. Despite the pro-angiogenic role of hCG, little is known about the endovascular interactions of trophoblasts and endothelial cells and its subsequent effects on spiral arteries especially in the presence of different forms of hCG. Recently we reported that injection of preeclampsia serum in pregnant IL-10$^{7"}$ mice results in hypertension and proteinuria. The treatment also led to a perturbed immune cell population at the maternal-fetal interface. Higher hCG levels in preeclampsia serum at term as compared to normal pregnancy serum has been reported. Several studies have reported a decrease in Treg cell population both in the circulation and in placental bed sections in preeclamptic women as compared to those with normal pregnancy. Since IL-10 and hCG are implicated in normal pregnancy outcome, it is tempting to speculate that deficiency in these molecules may predispose to severe preeclampsia pathology. Animal studies from our lab suggest that IL-10 deficient mice are more sensitive to serum- and hypoxia-induced onset of preeclampsia-like features.

All documents cited herein are incorporated by reference in their entirety as if fully set forth herein.

Reference is made to the following:

1. Cole L A. New discoveries on the biology and detection of human chorionic gonadotropin. *Reprod Biol Endocrinol* 2009; 7:8.
2. Cole L A Biological functions of hCG and hCG-related molecules *Reprod Biol Endocrinol* 2010:8:102.
3. Meekins, J. W., Pijnenborg, R., Hanssens, M., McFadyen, I. R, van Asshe, A., 1994. A study of placental bed spiral arteries and trophoblast invasion in normal and severe preeclamptic pregnancies. *Br J Obstet Gynaecol.* 101, 669-674.
4. Toldi, G. Svec P, Vasarhelyi B, Meszaros G, Rigo J, Tulassay T, Treszi. A. Decreased number of FoxP3+ regulatory T cells in preeclampsia. *Acta Obstet Gynecol Scand* 2008; 87:1229-33.
5. Williams P J, Bulmer J N, Searle R F, Innes B A, Robson S C. Altered decidual leucocyte populations in the placental bed in pre-eclampsia and foetal growth restriction: a comparison with late normal pregnancy. *Reproduction* 2009; 138:177-184.
6. Stenman U H, Tiitinen A, Alfthan H, Valmu L. The classification, functions and clinical use of different isoforms of HCG. *Hum Reprod Update* 2006; 12:769-84.
7. de Medeiros S F, Norman R J. Human choriogonadotropin protein core and sugar branches heterogeneity: basic and clinical insights. *Hum Reprod Update* 2009:15:69-95.
8. Cole L A, Kardana A, Andrade-Gordon P, Gawinowicz M A. Morris J C, Bergert E R, O'Connor J, Birken S. The Heterogeneity of Human Chorionic Gonadotropin (hCG). III. The Occurrence and Biological and Immunological Activities of Nicked hCG. *Endocrinology* 1991; 129: 1559-1567
9. Butler S A, Cole L A, Chard T, lies R K. Dissociation of human chorionic gonadotropin into its free subunits is dependent on naturally occurring molecular structural variation, sample matrix and storage conditions. *Ann Clin Biochem* 1998; 35 (Pt 6):754-60.
10. Kovalevskaya G, Kakuma T, Schlatterer J, O'Connor J F. Hyperglycosylated HCG expression in pregnancy: cellular origin and clinical applications. *Mol Cell Endocrinol* 2007; 260-262237-43.
11. Elliott M M, Kardana A, Lustbader J W, Cole I. A. Carbohydrate and peptide structure of the alpha- and beta-subunits of human chorionic gonadotropin from normal and aberrant pregnancy and choriocarcinoma. *Endocrine* 1997; 7:15-32.
12. Cole L A. Hyperglycosylated hCG. *Placenta* 2007; 28:977-86.

13. Jeschke U, Stahn R. Goletz C, Wang X, Briese V, Friese K, hCG in trophoblast tumour cells of the cell line Jeg3 and hCG isolated from amniotic fluid and serum of pregnant women carry oligosaccharides of the sialyl Lewis X and sialyl Lewis a type. *Anticancer Res.* 2003; 23(2A):1087-1092.

14. Jeschke U, Toth B, Scholz C, Friese K, Makrigiannakis A. Glycoprotein and carbohydrate binding protein expression in the placenta in early pregnancy loss. *J Reprod Immunol* 2010; 85:99-105.

15. Stahn R, Goletz S, Stahn R, Wilmanowski R, Wang X, Briese V. Friese K, Jeschke U. Human chorionic gonadotropin (hCG) as inhibitor of E-selectin-mediated cell adhesion. *Anticancer Res.* 2005; 25:1811-1816.

16. Somerset D A, Zheng Y, Kilby M D, Sansom D M, Drayson M T. Normal human pregnancy is associated with an elevation in the immune suppressive CD25+ CD4+ regulatory T-cell subset. *Immunology* 2004; 1 12:38-43.

17. Aluvihare V R, Kallikourdis M, Betz A G. Regulatory T cells mediate maternal tolerance to the fetus. *Nat Immunol.* 2004; 5(3):266-71.

18. Robertson S A, Guerin L R, Bromfield J J, Branson K M, Ahlstrom A C, Care A S. Seminal fluid drives expansion of the CD4+CD25+ T regulatory cell pool and induces tolerance to paternal alloantigens in mice. *Biol Reprod* 2009; 80(5):1036-45.

19. Schumacher A, Brachwitz N. Sohr S. Engeland K. Langwisch S, Dolaptchieva M, Alexander T, Taran A. Malfertheiner S F. Costa S D, Zimmermann G, Nitschke C, Volk H D, Alexander H, Gunzer M, Zenclussen A C Human chorionic gonadotropin attracts regulatory T cells into the fetal-maternal interface during early human pregnancy. *J Immunol* 2009; 182:5488-97

20. Hanna N, Hanna 1, Hleb M, Wagner E, Dougherty J, Balkundi D, Padbury J, Sharma S. Gestational age-dependent expression of IL-10 and its receptor in human placental tissues and isolated cytotrophoblasts. *J Immunol* 2000; 164:5721-8.

21. Thaxton J E, Romero R, Sharma S. TLR9 activation coupled to IL-10 deficiency induces adverse pregnancy outcomes. *J Immunol* 2009; 183(2):1 144-54

22. Murphy S P, Hanna N N, Fast L D, Shaw S K, Berg G, Padbury J F, Romero R, Sharma S. Evidence for participation of uterine natural killer cells in the mechanisms responsible for spontaneous preterm labor and delivery. *Am J Obstet Gynecol.* 2009; 200(3):308.e1-9.

23. Groux H, O'Garra A, Bigler M, Rouleau M, Antonenko S, de Vries J E, Roncarolo M G. A CD4+ T-cell subset inhibits antigen-specific T-cell responses and prevents colitis. *Nature* 1997; 389:737-42.

24. Baban B, Chandler P R, Sharma M D, Pihkala J, Koni P A, Munn D H, Mellor A L. IDO activates regulatory T cells and blocks their conversion into Th17-like T cells. *J Immunol* 2009; 183:2475-83.

25. Wan H, Versnel M A, Cheung W Y, Leenen P J, Khan N A, Benner R, Kiekens R C. Chorionic gonadotropin can enhance innate immunity by stimulating macrophage function. *J Leukoc Biol* 2007; 82:926-33.26. Berndt S, Perrier d'Hauterive S, Blacher S. Pequeux C, Lorquet S, Munaut C, Applanat M. Herve M A. Lamande N, Corvol P, van den Brule F, 26. Frankenne F, Poutanen M, Huhtaniemi I, Geenen V, Noel A, Foidart J M. Angiogenic activity of human chorionic gonadotropin through LH receptor activation on endothelial and epithelial cells of the endometrium. *FASEB J* 2006; 20(14):2630-2

27. Herr F, Baal N, Reisinger K, Lorenz A, McKinnon T. Preissner K T. Zygmunt M. HCG in the regulation of placental angiogenesis. Results of an in vitro study. *Placenta.* 2007 April; 28 Suppl A:S85-93.

28. Cray B A, Esadeg S, Chantakru S, van den Heuvel M. Pattaro V A, He H, Black G P, Ashkar A A, Kiso Y, Zhang J. Update on pathways regulating the activation of uterine Natural Killer cells, their interactions with decidual spiral arteries and homing of their precursors to the uterus. J Reprod Immunol 2003; 59.175-91.

29. Manaster I, Mandelboim O. The unique properties of uterine N K cells. *Am J Reprod Immunol* 2010: 63:434-44.

30. Kalkunte S S, Mselle T F, Norris W E. Wira C R, Sentman C L, Sharma S. Vascular endothelial growth factor C facilitates immune tolerance and endovascular activity of human uterine N K cells at the maternal-fetal interface. *J Immunol* 2009; 1 82:4085-92.

31. Kane N, Kelly R, Saunders P T, Critchley H O. Proliferation of uterine natural killer cells is induced by human chorionic gonadotropin and mediated via the mannose receptor. Endocrinology 2009, 1 50:2882-8

32. Roberts J M, Hubel C A. Is oxidative stress the link in the two-stage model of preeclampsia. *Lancet* 1 999; 354: 788-789.

33. Kalkunte S, Boij R, Norris W. Friedman J. Lai Z, Kurtis J, Lim K H, Padbury J F, Matthiesen L. Sharma S. Sera from preeclampsia patients elicit symptoms of human disease in mice and provide a basis for an in vitro predictive assay. *Am J Pathol.* 2010, 177(5):2387-98.

34. Kalkunte S, Nevers T, Norris W, Banerjee P, Fazleabas A, Kuhn C, Jeschke U, Sharma S. Presence of non-functional hCG in preeclampsia and rescue of normal pregnancy by recombinant hCG. Placenta. 2010, 31. A1 26.35.

35. Sasaki Y, Darmochwal-Kolarz D, Suzuki D, Sakai M. Ito M, Shima T, Shiozaki A, Rolinski J, Saito S. Proportion of peripheral blood and decidual CD4(+) CD25 (bright) regulatory T cells in pre-eclampsia. *Clin Exp Immunol* 2007, 149:139-45.

36. Santner-Nanan B. Peek M J, Khanam R, Richarts L, Zhu E, Fazekas de St Groth B, Nanan R. Systemic increase in the ratio between Foxp3+ and IL-17-producing CD4+T cells in healthy pregnancy but not in preeclampsia. *J Immunol* 2009; 183:7023-30.

37. Prins J R, Boelens I-M, Heimweg J, Van der Heide S, Dubois A E, Van Oosterhout A J, Erwich J J. Preeclampsia is associated with lower percentages of regulatory T cells in maternal blood. *Hypertens Pregnancy* 2009; 28:300-11.

38. Lai Z. Kalkunte S. Sharma S. Pregnancy-specific effects of hypoxia: a mouse model for preeclampsia. *Am J Reprod Immunol* 2009; 61: 398

39. Lai Z, Kalkunte S, Sharma S. A critical role of IL-10 in modulating hypoxia-induced preeclampsia-like disease in mice. Hypertension. 2011.

40. WO0070094, "Methods For Predicting Pregnancy Outcome In A Subject By hCGg Assay" John O'connor et al 41. WO2011100462/us201 1201 122 "Hyperglycosylated hCG Detection Device," Albert R. Nazareth et al.

42. U.S. Pub No 20100129935 "Pregnancy Testing Method," Sarah Maddison

43. U.S. Pub. No. 20080241958. "Method for Determining hCG Levels in Fluid Samples," Hsiao-Ching Yee et al 44. US Pub. No. 2006010541 1 Method Of Detecting Early Pregnancy At High Accuracy By Measuring hCG And Hyperglycosylated hCG Concentrations Equally by Laurence A Cole 45. U.S. Pat. No. 7,572,639 Method And Apparatus For Predicting Pregnancy Outcome, Laurence A Cole et al"
45. WO0061638 "Prenatal Screening for Down's Syndrome Using Hyperglycosylated Gonadotropin," Laurence A. Cole et al.
47. *Bioassay Techniques for Drug Development*, Rahman, et al, (Informa Healthcare (2001)).
48. *Assay Development: Fundamentals and Practices*. Ge Wu, (Wiley (2010)).
49. *Pre-eclampsia: Etiology and Clinical Practice*, Lyall et al., (Cambridge University Press (2010))
50. *The Diagnosis and Management of Pre-eclampsia and Eclampsia*, O'Loughlin et al. (Institute of Obstetricians and Gynaecologists, Royal College of Physicians of Ireland (Version 1.0. Guideline No. 3, 2011).

SUMMARY OF THE INVENTION

Disclosed herein is a method of determining incipient preeclampsia at an early stage of pregnancy. Early is understood to include from about 20 weeks of pregnancy or earlier, or about 15, weeks or earlier or 10 weeks or earlier. The method comprises the steps of (a) performing a bioassay to determine the level of at least one sialyl Lewis antigen in a said patient-subject at about 25 weeks of pregnancy or earlier;

(b) performing a bioassay to determine the level of at least one sialyl Lewis antigen in a pregnant non-preeclampsia one or more subjects at about 30 weeks of pregnancy or later, wherein said at least one sialyl Lewis antigen assay is for a sialyl Lewis antigen assayed in step (a) is and if more than one subject is assayed, averaging said results;

(c) managing said patient-subject for preeclampsia, if said level of at least one sialyl Lewis antigen of step (a) is at or greater than about 20% above the level of such silalyl Lewis antigen assayed in step (b).

In some embodiments of this method the above noted determination of incipient preeclampsia is made at about at 25 weeks of pregnancy or earlier; about 15 weeks or earlier, 12 to 14 weeks or earlier, at about 10 weeks or earlier and at about 1 week. In some embodiments the determination of step (b) with diagnoses of either pre-eclampsia or non-preeclampsia female is made at about 32 weeks of pregnancy or later.

Also disclosed is a method of determining comparators of a diagnosis of incipient preeclampsia at 20 weeks of pregnancy or earlier by the steps of (a) determining the level of sialyl Lewis antigen in a female subject with a diagnosis of preeclampsia about 30 weeks of pregnancy or later, and, (b) determining the level of sialyl Lewis antigen in a pregnant non-preeclampsia female subject at about 30 weeks of pregnancy or later.

BRIEF DESCRIPTION OF THE DRAWINGS

FIG. 513 is a graph of production of sFlt-1.

DETAILED DESCRIPTION OF THE INVENTION

Figure 1:
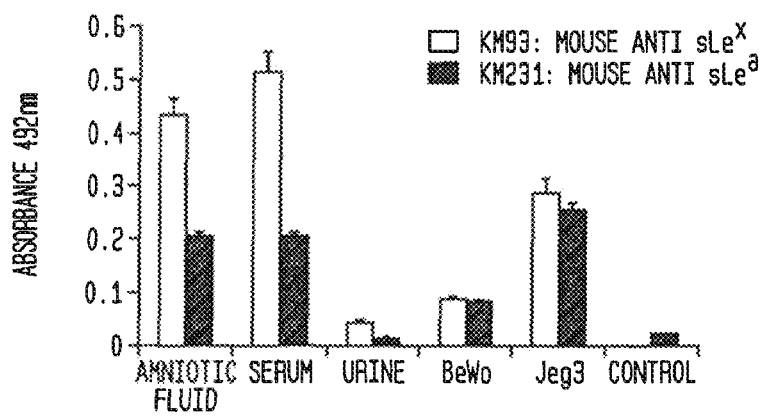
FIG. 1 is a graph of serum and amniotic fluid hCG exhibiting expression of sLex and sLea as compared to urine hCG and hCG secreted in supernatants from choriocarcinoma cells BeWo or Jeg 3.

In the practice of this invention it is to be understood that the detection of PE (or related GPs) in instances where the pathology is effectively treated is the detection of precursor indicia before 20 weeks of gestation. For convenience the notation "sLe<20w" is used to denote sialyl Lewis antigen elevation before 20 weeks of pregnancy. In this context, "elevation" will be understood to mean up-regulation or increase of at least about 20% of each of sialyl Lewis antigen alone as compared to the average control of the respective sialyl Lewis antigen, or more than 30% if two sialyl Lewis antigen levels are combined, and 50% increase if three are combined. There are a number of bioassays suitable to determine such levels and other assays are being developed.

The practice of the invention, in one embodiment, is characterized by finding altered carbohydrate patterns, with specific reference to by the excess or elevated presence of sialyl Lewis antigens on preeclampsia hCG as compared to normal pregnancy hCG Another aspect is the therapeutic use of sialyl Lewis antigen-free hCG in mitigating the symptoms associated with pregnancy complications such as preeclampsia. (*Expert Opin Drug Deliv.* 2012 August; 9(8):893-900. Epub 2012 Jun. 18.)

hCG Can Rescue Pregnancy.

Without being bound by any particular theory, in IL-10" mice, it is believed that the mode of action is by subverting production of anti-angiogenic factors and by replenishing uterine immune cells. Deglycosylated hCG is not reported as able to bind to mannose receptors on uNK cells, again emphasizing the importance of carbohydrate patterns in the function of hCG. Given the functional associations co-regulated by hCG, IL-10 and Treg migration, dysregulated hCG effects uterine Tregs and contributes to preeclampsia. Particularly noted is therapeutic administration of CG. CH with a less antigenic presentation is useful. This includes recombinant hCG. Intravenous administration is noted. Dosing with recombinant hCG, i.v. from between about 50 I.U. to about 500 I.U with particular reference to dosages between about 100 I.U and 200 I.U. is noted. Prefilled pens for administration of recombinant human chorionic gonadotropin (r-hCG) are available and useful in the practice of this invention.

EXEMPLIFICATION

Example 1

Quantification of Sialyl Lewis Antigens on hCG in Different Biological Fluids

Ninety-six-well microtitre plates (Maxisorp, Nunc) were coated with 50 µl rabbit anti-human hCG antibody (5 µg/ml in PBS, Dako A0231) at 4° C. overnight. The wells were washed three times with PBS, pH 7.2 containing 0.05% Tween 20, blocked for 1 hour with washing buffer containing 1% BSA and washed again three times.

50 µl of pregnancy serum/amniotic fluid/urine/cell culture supernatant samples or hCG (5 µg/ml) were added and incubated for 1.5 hours at room temperature and washed three times. 50 µl of sLe$^x$ (Calbiochem, KM93) or sLe$^a$ (Calbiochem, KM 231) recognizing antibodies were added at concentration of 1 µg/ml. The wells were incubated for 1.5 hours at room temperature and washed three times 50 µl of HRP-conjugated rabbit anti-mouse antibody (Dako, PO260) was added to each well, incubated for 1.5 hours, washed three times, developed with DMB and color development was followed by measuring the absorbance at 492 nm/630 nm Wells without hCG served as controls.

Example 2

Quantification of Sialyl Lewis Antigens from Preeclampsia Serum hCG and Normal Pregnancy Serum hCG Ninety-six-well microtitre plates (Maxisorp, Nunc) were coated with 50 µl rabbit anti-human hCG antibody (5 µ9/ιτιI in PBS, Dako A0231) at 4° C. overnight. The wells were washed three times with PBS, pH 7.2 containing 0.05% Tween 20, blocked for 1 hour with washing buffer containing 1% BSA and washed again three times.

50 µl of human normal (n=15) or preeclampsia diagnosed pregnancy serum (n=14) obtained from blood collected at 32-36 weeks of pregnancy were added and incubated for 1.5 hours at room temperature and washed three times.

50 µl of sLe$^x$ (Calbiochem, KM93) or sLe$^a$ (Calbiochem, KM 231) or Le$^y$ or Thomsen-Friedenreich antigen (Glycotope) recognizing antibodies were added at concentration of 5 µg/ml in PBS. The wells were incubated for 1.5 hours at room temperature and washed three times.

50 µl of HRP-conjugated rabbit anti-mouse antibody (Dako, PO260) was added to each well, incubated for 1.5 hours, washed three times, developed with DMB and color development was followed by measuring the absorbance at 492 nm/630 nm. The mean absorbance obtained with multiple normal pregnancy hCG were considered as 100%.

Figure 2:
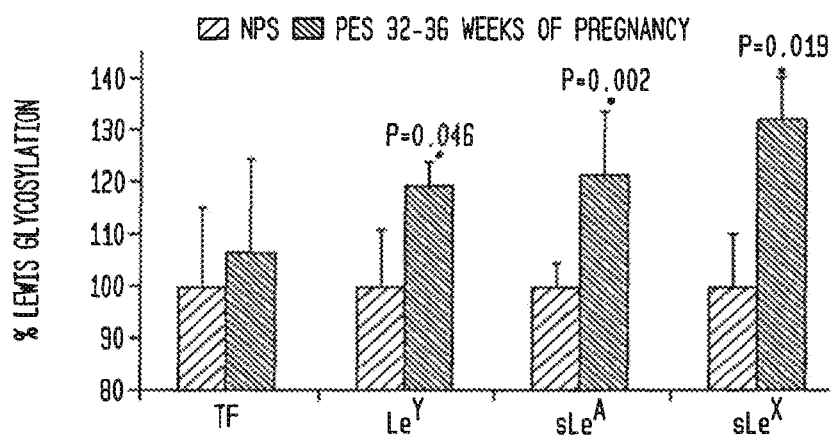
FIG. 2. is a graph of sialyl Lewis antigen (sLe$^Y$, sLe$^a$ and sLe$^x$) expression on preeclampsia serum (PES)-hCG as compared to normal pregnancy serum (NPS)-hCG.

As seen in the FIG. 2, sialyl Lewis antigen (LeY, sLeA and sLeX) expression is significantly higher on preeclampsia serum (PES)-hCG as compared to normal pregnancy serum (NPS)-hCG As seen in FIG. 2, there was 21.6% up-regulation of sLe$^a$ (P=0.002), 32% up-regulation of sLe$^x$ (P=0.019) and 21.6% up-regulation of Le$^Y$ in the 32nd-36th week of gestation (P=0.021) in preeclamptic hCG compared to normal pregnancy hCG. The increase in sialyl Lewis antigen expression in PES-hCG was independent of the serum levels of β-hCG.

Example 3

Quantification of Sialyl Lewis Antigens in Serum hCG Collected Before the Onset of Preeclampsia Ninety-six-well microtitre plates (Maxisorp, Nunc) were coated with 50 µl rabbit anti-human hCG antibody (5 µ9/ιηI in PBS, Dako A0231) at 4° C. overnight. The wells were washed three times with PBS, pH 7.2 containing 0.05% Tween 20, blocked for 1 hour with washing buffer containing 1% BSA and washed again three times.

50 µl of human serum obtained from blood collected at 12-14 weeks of pregnancy who later either went on have normal pregnancy (n=8) or were diagnosed with preeclampsia (n=8) were added and incubated for 1.5 hours at room temperature and washed three times. 50 µl of sLe$^x$ (Calbiochem. KM93) or sLe$^a$ (Calbiochem, KM 231) or Le$^y$ or Thomsen-Friedenreich (TF) antigen (Glycotope) recognizing antibodies were added at concentration of 5 µg/ml in PBS.

The wells were incubated for 1.5 hours at room temperature and washed three times. 50 µl of HRP-conjugated rabbit anti-mouse antibody (Dako, PO260) was added to each well, incubated for 1.5 hours, washed three times, developed with DMB and color development was followed by measuring the absorbance at 492 nm/630 nm. The mean absorbance obtained with multiple normal pregnancy hCG were considered as 100%.

Figure 3:
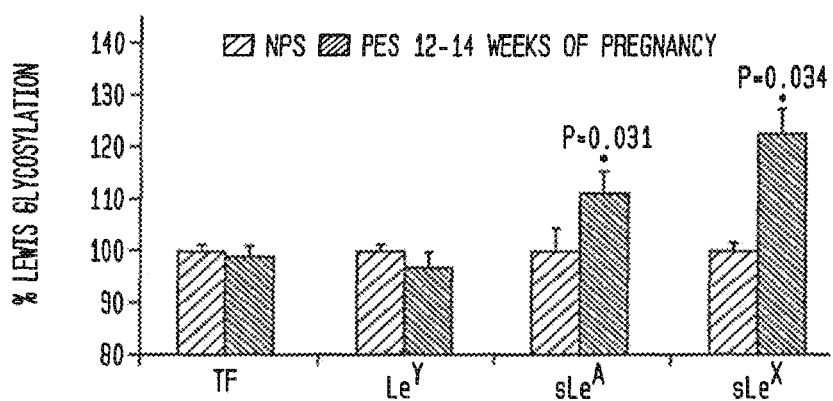
FIG. 3 is a graphic quantification of sialyl Lewis antigens in serum.

As seen in the FIG. 3, sialyl Lewis antigen (sLe$^a$ and sLe$^x$) expression is significantly elevated on preeclampsia serum (PES)-hCG collected at 12-14 weeks of pregnancy before the clinical diagnosis of disease as compared to normal pregnancy serum (NPS)-hCG. The increase in sialyl Lewis antigen expression in PES-hCG was independent of the serum levels of β-hCG. 11.2% upregulation in SLe$^a$ and 22.4% upregulation in SLe$^x$ expression in the 10th-12th week of gestation in preeclamptic hCG compared to normal pregnancy hCG. The expression of the TF antigen is not significantly changed in preeclamptic hCG compared to normal control hCG.

Example 4

Rescue of Preeclampsia-Like Features (IUGR, Hypertension and Proteinuria) by Sialyl Lewis Antigen-Free hCG (Functional hCG) in Mouse Model Pregnant IL-10$^{7"}$ mice were injected (gestational day 10, i.p) with either normal pregnancy serum (NPS) or PE serum (PES) with or without sialyl Lewis antigen-free hCG (urine or recombinant).

On gestational day 17, blood pressure and fetal weight were recorded Urinary albumin and creatinine was measured in 24-hour urine samples using commercial ELISA kits. Proteinuria is expressed as a ratio of albumin and creatinine.

Figure 4A:
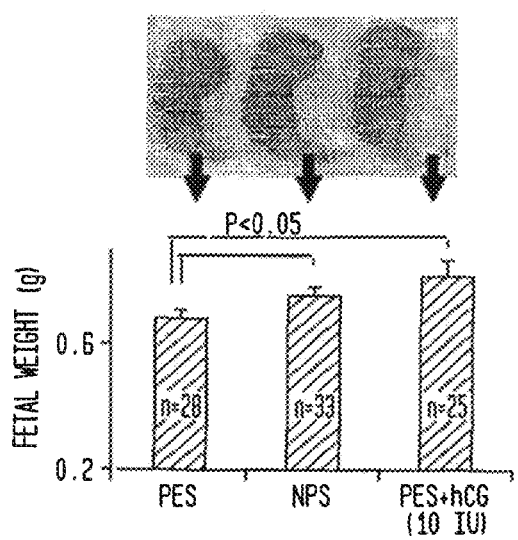
FIG. 4A are displays fetal size (upper panel) and fetal weights (lower panel).
Figure 4B:
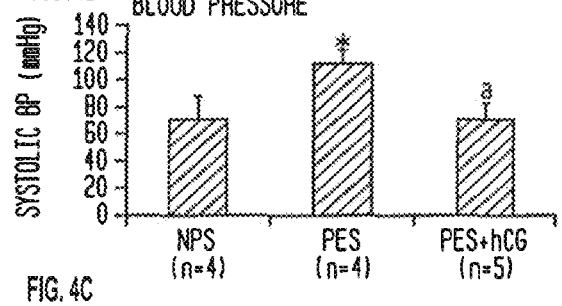
FIG. 4B presents blood pressure data
Figure 4C:
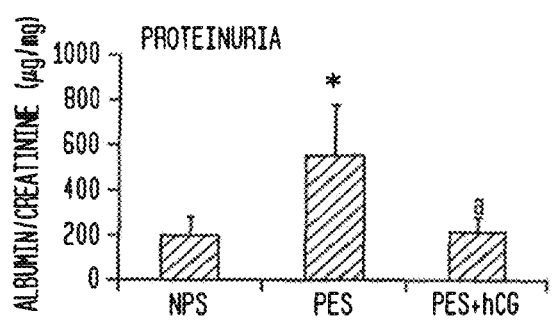
FIG. 4C presents mouse subject proteinuria levels.

As seen in FIG. 4, functional hCG treatment reverses PES-induced intrauterine growth restriction (IUGR) (A) as reflected by fetal size (upper panel) and fetal weights (lower panel), hypertension (B), and proteinuria (C) in pregnant IL-10$^{7"}$ mice. * and $^a$P<0.05 significance as compared to NPS and PES groups respectively by student's T test Example 5

Rescue of Preeclampsia-Like Features (Kidney Pathology, Elevated Soluble Flt-1 and Soluble Endoqiin) by Sialyl Lewis Antigen-Free hCG (Functional hCG) in Mouse Model Pregnant IL-10$^{7"}$ mice were injected (gestational day 10, i.p) with either NPS or PES with or without sialyl Lewis antigen-free hCG (urine or recombinant).

On gestational day 17, blood was collected by cardiac puncture and serum separated. Serum levels of mouse sFlt-1 & sEng were measured using commercial ELISA kits (R&D Systems).

Figure 5A:
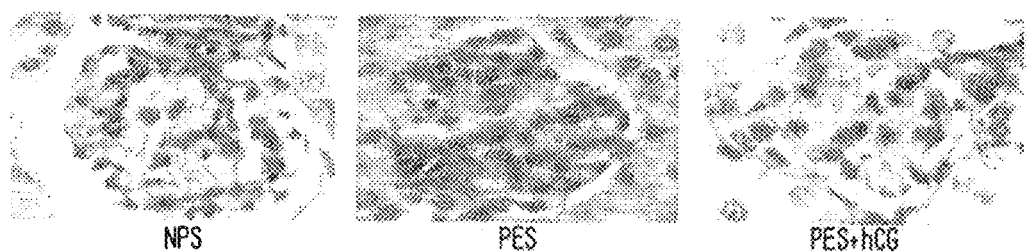
FIG. 5A shows renal pathology by H&E staining of the glomerulus
Figure 5B:
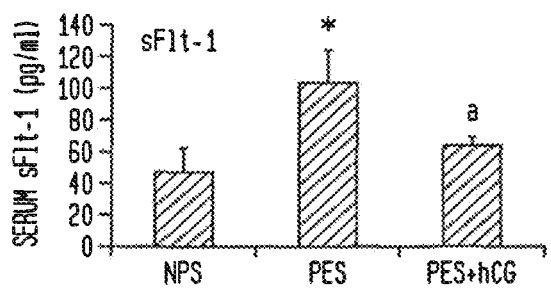
FIG. 5C is a graph of sEng in pregnant IL-10$^{7"}$ mice.
Figure 5C:
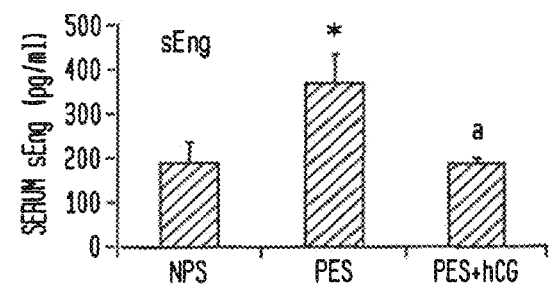

As seen in FIG. 5, functional hCG treatment reverses PES-induced renal pathology as shown by H&E staining of glomerulus (A), and excess production of sFlt-1 (B) and sEng (C) in pregnant IL-10$^{7"}$ mice. * and $^a$P<0.05 significance as compared to NPS and PES groups respectively by student's T test

Example 6

Treatment of Pregnant Human with Sialyl Lewis Antigen Elevation Before 20 Weeks of Pregnancy A 26 year old female presents at 10 weeks of pregnancy. Her serum is tested by the method of Example 2. The test detects sialyl Lewis antigen $sLe^Y$ levels above 25% average control normal.

These results are consistent with and predictive of consistent with incipient PE. She is then dosed with recombinant 100 IU hCG, i.v. The pregnancy comes to term without either insufficient trophoblast invasion or marked maternal spiral artery remodeling and inflammation.

Example 7

Treatment of Pregnant Human with Sialyl Lewis Antigen Elevation Before 20 Weeks of Pregnancy A 26 year old female presents at 10 weeks of pregnancy. Her serum is tested by the method of Example 2. The test detects sialyl Lewis antigen $sLe^Y$ level of 18% above average control normal, and $sLe^x$ level of 18% above average control normal, and $sLe^a$ level of 15% above average control normal, with a combined percentage of over 50% above average control. These results are consistent with and predictive of incipient PE. She is then managed for preeclampsia. The pregnancy comes to term without either insufficient trophoblast invasion or marked maternal spiral artery remodeling and inflammation.

The invention claimed is:

1. A method of treating incipient preeclampsia in a human-female patient-subject by
   (a) determining the level of sialyl Lewis antigen A in said patient-subject at about 10 weeks of pregnancy or earner;
   (b) determining that said level of sialyl Lewis antigen A of step (a) is at or greater than about 11.2% above a normal control level; and
   (c) administering to said patient-subject a therapeutically effective amount of human chorionic gonadotropin (hCG):
   thereby treating the human female patient-subject for incipient preeclampsia.

2. The method of claim 1, further comprising: prior to administering the hCG of step (c), managing said patient-subject for preeclampsia.

3. The method of claim 1, wherein the hCG is recombinant hCG.

4. The method of claim 1, wherein the therapeutically effective amount of hCG is administered intravenously.

5. The method of claim 1, wherein the therapeutically effective amount of hCG is from between about 50 I.U. and about 500 I.U.

6. The method of claim 5, wherein the therapeutically effective amount of hCG is from between about 100 I.U. and about 200 I.U.

\* \* \* \* \*